(12) United States Patent
Miotti et al.

(10) Patent No.: US 6,771,738 B2
(45) Date of Patent: Aug. 3, 2004

(54) METHOD AND APPARATUS FOR OBTAINING AN IMAGE BY RADIOGRAPHY WITH AN ANTI-SCATTER GRID

(75) Inventors: Luc Miotti, Vanves (FR); Serge Muller, Guyancourt (FR); Andreas Rick, Schwerte (DE)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 22 days.

(21) Appl. No.: 10/127,079

(22) Filed: Apr. 18, 2002

(65) Prior Publication Data

US 2002/0196902 A1 Dec. 26, 2002

(30) Foreign Application Priority Data

Apr. 30, 2001 (FR) .......................................... 01 05822

(51) Int. Cl.[7] ................................................ G21K 1/00
(52) U.S. Cl. ........................................ 378/155; 378/154
(58) Field of Search ................................. 378/154, 155

(56) References Cited

U.S. PATENT DOCUMENTS

| | | | |
|---|---|---|---|
| 4,773,087 A | 9/1988 | Plewes | 378/146 |
| 4,803,716 A | 2/1989 | Ammann et al. | 378/155 |
| 5,054,048 A | 10/1991 | Wang | 378/146 |
| 5,357,554 A | 10/1994 | Schneiderman et al. | 378/155 |
| 6,181,773 B1 * | 1/2001 | Lee et al. | 378/155 |
| 6,304,632 B1 * | 10/2001 | Rick et al. | 378/155 |
| 6,535,577 B2 * | 3/2003 | Mioitti et al. | 378/155 |

FOREIGN PATENT DOCUMENTS

| | | |
|---|---|---|
| EP | 0063644 | 11/1982 |
| EP | 0494489 | 4/2000 |

* cited by examiner

*Primary Examiner*—Edward J. Glick
*Assistant Examiner*—Courtney Thomas
(74) *Attorney, Agent, or Firm*—Jay L. Chaskin; Cantor Colburn LLP

(57) ABSTRACT

Method and apparatus for a radiographic image of an object obtained by a radiography apparatus containing an X-ray emitter, in which an anti-scatter grid placed between the object and a radiographic image receiver is displaced, on rectilinear translation in its plane, when acquiring the images, between a starting position and an arrival position, according to a time displacement law of reference, at a greater rate of displacement in proximity to a starting position and to the arrival position. A measurement of the energy received in the form of X-radiation by the receiver is used to modify the rate of displacement of the grid at every instant.

18 Claims, 3 Drawing Sheets

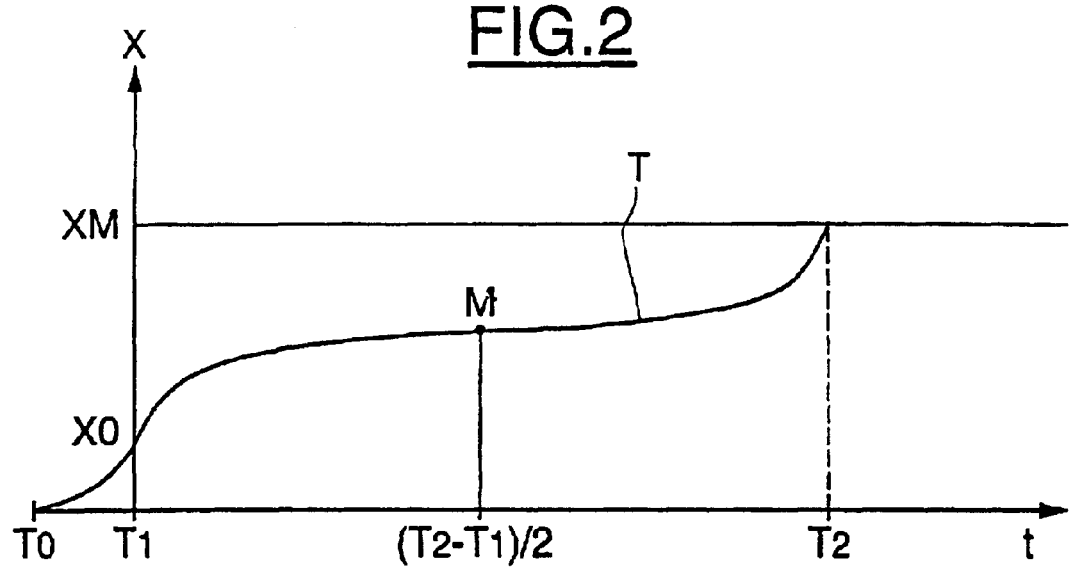
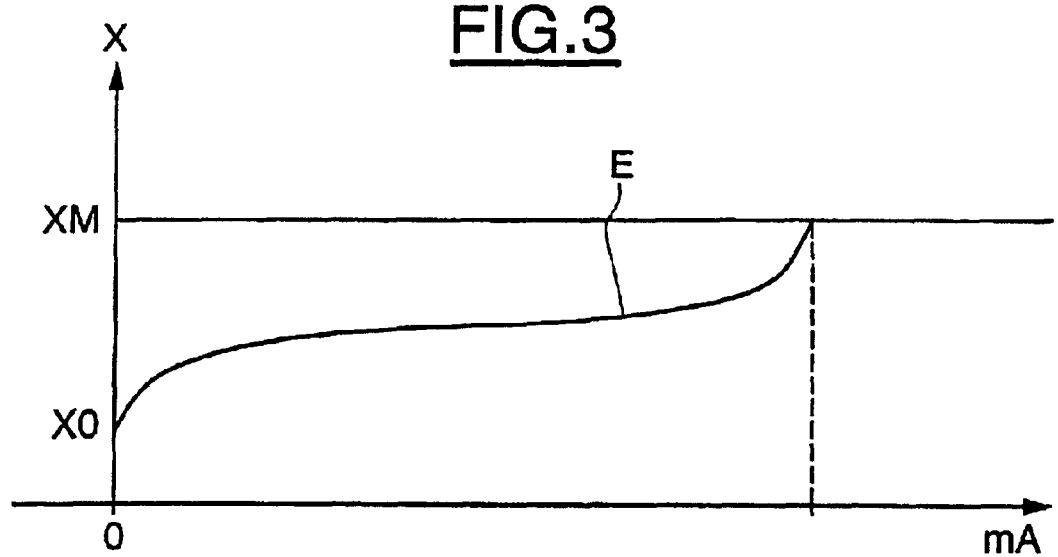

METHOD AND APPARATUS FOR OBTAINING AN IMAGE BY RADIOGRAPHY WITH AN ANTI-SCATTER GRID

CROSS-REFERENCE TO RELATED APPLICATION

This application claims the benefit of a priority under 35 USC 119 to French Patent Application No. 0105822 filed Apr. 30, 2001, the entire contents of which are hereby incorporated by reference.

BACKGROUND OF THE INVENTION

The invention is directed to a method and apparatus for a radiographic image of an object obtained by a radiography apparatus having an anti-scatter grid.

The invention may be applied but not exclusively to mammography examinations, principally for the detection of microcalcifications inside a breast.

A radiography apparatus, as generally used in mammography, is equipped with an anti-scatter grid placed between the object to be X-rayed, in this case a breast, and a receiver of X-ray images. The anti-scatter grid comprises a series of plates spaced apart and directed toward the focal point of an X-ray beam emitted toward the object and an image receiver. Thus, the anti-scatter grid lets unscattered direct beams pass, while the scattered beams are absorbed by the plates.

The resolution of the image receiver is generally finer than the spacing between two plates, which is typically in the order of 0.3 mm. As a result, the plates are visualized on the radiographic image obtained. This visualization interferes with the mammography, as it renders more difficult the detection of microcalcifications, and principally microcalcifications associated with pathological lesions.

One known solution comprises displacing the grid during exposure, in rectilinear translation in its plane, that is, roughly perpendicular to the plates of the anti-scatter grid. Such a translation can be carried out solely in one direction, or alternatively in both directions. The image quality is thus improved, but still remains insufficient. Furthermore, the generation of an alternating motion is a relatively complex mechanical solution.

Patent FR 2,784,569 discloses a method for a radiographic image of an object obtained by a radiography apparatus equipped with an anti-scatter grid driven in translation according to a time displacement law. The time displacement low is a continuous curve presenting a point symmetry in relation to the point whose time coordinate is equal to half the duration of exposure and whose time variable spatial derivative presents two symmetrical linear portions in relation to an axis of symmetry passing through the middle of the range of displacement of the grid. This method proves satisfactory in case the instantaneous energy supplied by the emitter in the form of X-radiation is known with precision and is constant during the period of exposure. The quality of the image supplied by the receiver depends on the quantity of energy received in the form of X-radiation by the receiver upon the period of exposure. Known techniques do not make it possible to obtain an X-radiation source possessing an instantaneous energy level of the X-radiation emitted, determined with precision and constant. As a result, the plates of the anti-scatter grid are still visible to some extent.

BRIEF DESCRIPTION OF THE INVENTION

An embodiment of the invention proposes eliminating the visible traces of the plates of the anti-scatter grid on the X-ray film as much as possible. An embodiment of the invention proposes obtaining an improvement of image quality with mechanically simple means for displacement of the anti-scatter grid.

According to an embodiment, the invention is a method and apparatus for a radiographic image of an object obtained by a radiography apparatus containing an X-ray emitter, in which an anti-scatter grid placed between the object and a radiographic image receiver is displaced, on rectilinear translation in its plane, on shooting of images, between a starting position and an arrival position, according to a predefined time displacement law, at a greater rate of displacement in proximity to a starting position and to an arrival position than between those two positions. A measurement of the energy received in the form of X-radiation by the receiver is used to modify the rate of displacement of the grid at every instant. Thus, the displacement of the anti-scatter grid can be adjusted to the energy received by the receiver, so that, during the exposure time, each part of the receiver has been exposed to substantially the same quantity of X-radiation energy, apart from the rays absorbed by the object studied itself. The energy received by the receiver is measured from the energy emitted by the X-ray emitter. The energy received in the form of X-rays by the receiver is measured from the energy coming to the receiver.

An embodiment of the invention is directed to a radiographic imaging device, comprising means for providing an X-ray emitter, means for receiving the X-rays after having crossed an organ to be studied, an anti-scatter grid movable in translation in a plane roughly perpendicular to the X-rays, means for displacement capable of producing the displacement of the anti-scatter grid in its plane on shooting of the image, between a starting position and an arrival position, according to a predefined time displacement law, means for computing, means for measurement of the energy received by the means for receiving in the form of X-rays, and means for modifying the predefined time displacement law. The means for computing is connected to the means for measurement. The means for computing is capable of emitting a control signal to the means for displacement. The data received by the means for computing from the means for measurement can make a correction to the speed of the anti-scatter grid. According to an embodiment, the means for measurement is disposed on an energy supply link of the means for providing an emitter, in order to measure the energy actually emitted by the emitter. According to an embodiment, the means of measurement is disposed on the means for receiving in order to measure the energy actually received by the receiver.

BRIEF DESCRIPTION OF THE DRAWING

The invention will be better understood from the following description when read with drawings, in which:

FIG. 2 illustrates a time displacement law of an anti-scatter grid;

FIG. 3 illustrates a displacement law as a function of the energy received in the form of X-rays by a receiver;

DETAILED DESCRIPTION OF THE INVENTION

Figure 1:
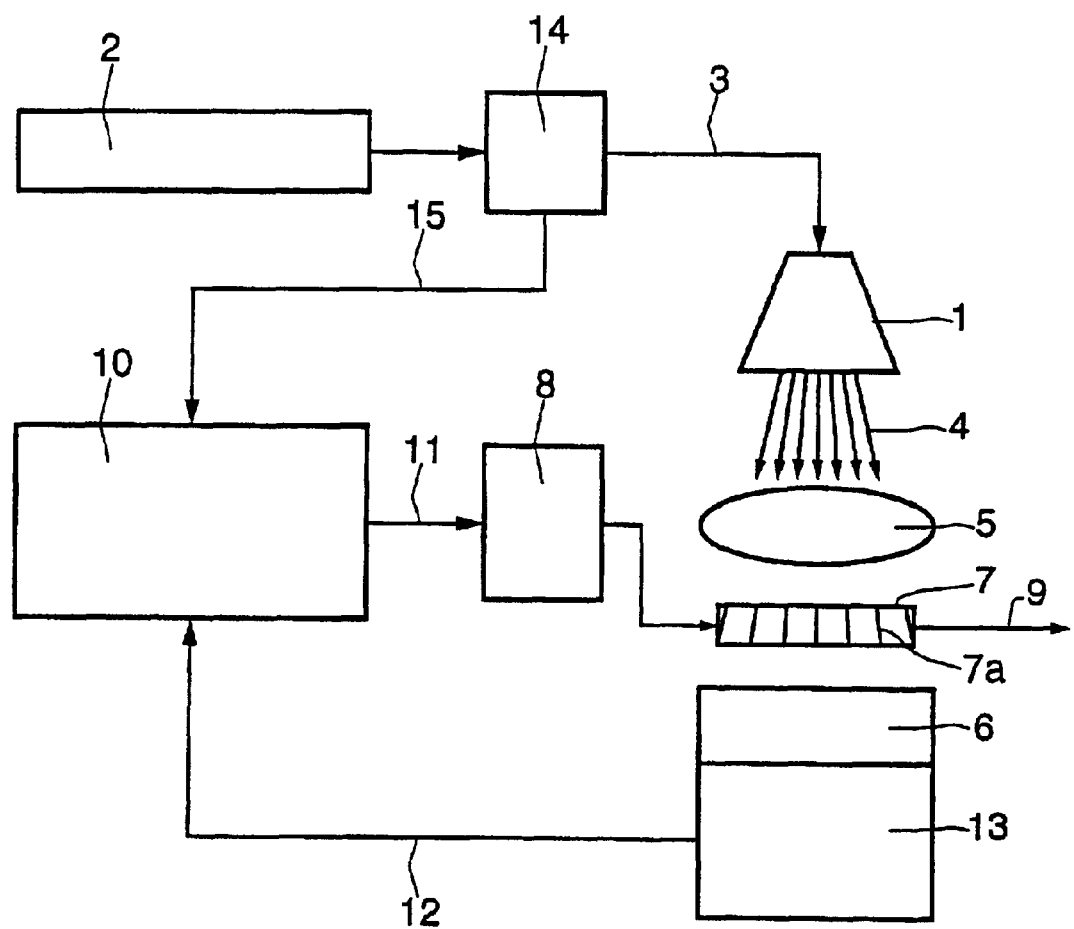
FIG. 1 is a schematic view of an apparatus for carrying out an embodiment of the method.

In FIG. 1, means for providing an X-ray emitter 1 is fed by an energy source 2 in the form of a high-voltage generator by means of a link 3. The emitter 1 may be an X-ray tube emitting an X-ray beam 4 from a focal point not represented on the figure, in the direction of an object 5 to be X-rayed, for example, a breast on a mammography examination. The radiographic images are received by means for receiving 6, comprising, for example, a matrix sensor of solid-state or CCD type with scintillator. Between the object 5 and the receiver 6 is arranged an anti-scatter grid 7. The anti-scatter grid is movable in translation in a plane roughly perpendicular to the X-ray beam emitted. The anti-scatter grid comprises a plurality of plates 7a spaced apart and directed toward the focal point of the emitter 1. The plates 7a, typically spaced 0.3 mm apart, absorb radiation scattered by the object 5 and let pass in the direction of the receiver 6 only the direct radiation having crossed the object 5 and having passed between two adjacent plates of the anti-scatter grid 7.

A means for displacement 8 for displacement of the grid 7 in translation in its plane, in the direction is indicated by an arrow 9. Means for computing 10 emits a control signal by means of a link 11 to the means for displacement 8, in order to control the rate of displacement of the anti-scatter grid 7. The means for computing 10 receives, through a link 12, data coming from a first means for measurement 13 of the X-radiation energy received by the receiver 6. The computer unit 10 also receives data, through a link 15, coming from a second means for measurement 14 of the energy supplied by the energy source 2. The means for measurement 14 is situated on link 3.

The computer unit 10 comprises at least one microprocessor, at least one memory, and at least one computer and/or control program stored in memory and capable of being executed by the microprocessor.

On radiographic imaging, in order to avoid visualization of the plates 7a on the images obtained, the grid 7 is displaced in rectilinear translation in its plane. The rate of displacement of the grid 7 varies according to a time law T of displacement of the grid 7 between a starting position X0 and an arrival position XM.

Assume that the "period" of the grid 7 designates the distance separating the edge of a plate 7a from the edge of the immediately adjacent plate 7a, that is, a distance equal to the thickness of a plate 7a plus the distance between two adjacent plates 7a. One of the main reasons for visualization of plates 7a on the radio-graphic images obtained, is because, on displacement of the grid, the number of periods of the grid passing between the X-ray beam and a pixel of the receiver 6 is not a whole number. As a result, some pixels possess a time of effective exposure to X-rays greater than neighboring pixels because of the period of the grid in motion.

If the plates 7a in a grid have the same width as the spacing between two adjacent plates 7a, two pixels at an approximate distance apart of a half-period in the direction of displacement of the grid will be exposed for an identical time on a displacement of the grid by a whole number of periods, that is, those pixels will have received the same quantity of energy and will therefore present an identical blackening, if it is assumed that the energy emitted by the X-ray beam is constant and that the rate of displacement of the grid is constant. Blackening of the pixels is a function of the quantity of energy received in X-ray form, which is the time integral of the instantaneous energy received in X-ray form. If the grid is displaced by a half-period, depending on the position of the pixels, there are situations where a pixel will be masked by a plate opposite the X-ray beam during the displacement of a half-period, and the other pixel will be exposed to the X-ray beam during the same displacement. The quantity of energy received and, therefore, the blackening of the pixels will be different.

The displacement of the grid by other than whole number of periods, causes the plates 7a of the grid 7 to appear on the radiographic image. The appearance of the plates on the image interferes with the interpretation of the radiographic images obtained, principally the observation of mammography images, and more particularly for detecting microcalcifications.

Displacing the grid 7 at a variable rate of displacement reduces the appearance of traces of the grid 7 on the radiographic images. During the period of exposure, the plates 7a of the grid file past the receiver 6. It is at the beginning of the exposure period, when emission of the X-ray beam is started or when it is stopped, that incomplete periods of the grid 7 can file past the receiver 6.

By increasing the rate of displacement of the grid in proximity to the starting position and to the arrival position, which correspond respectively to the beginning and end of the exposure period, the exposure time of incomplete periods is reduced in relation to the exposure time of complete periods. Blackening of the receiver 6 is therefore diminished during incomplete periods, and the appearance of plates 7a of the grid 7 on the radiographic images is thus reduced.

It is not necessary to provide for a high rate of displacement in the middle of the exposure period, since in that zone complete grid periods file past between the X-ray beam and the receiver 6.

By way of example, FIG. 2 illustrates a curve T representing a time displacement law of the grid 7. The time is shown on an abscissa axis. The position X of the grid in the direction of displacement defined by the arrow 9 is shown on an ordinate axis. On the graphic representation chosen, the abscissa axis intersects the ordinate axis for a time T1 corresponding to the start of the exposure period, that is, to the start of emission of an X-ray beam in the direction of the organ to be studied. Time T2 corresponds to the end of the exposure period. At time T1, a point of the grid taken as reference is situated at X0. At time T2, the same point is situated at XM. The exposure period is situated between T1 and T2. The exposure time is T2−T1.

During the exposure period, the time displacement law entails a high rate of dis-placement in proximity to the starting point X0 and arrival point XM, which is translated in FIG. 2 by a steep slope of curve T. The time displacement law entails a slower rate of displacement in the middle of the range of displacement, which is translated on curve T by a less steep curve in the median part. Curve T presents a point symmetry on the exposure period in relation to the time abscissa point M (T2−T1)/2.

Between a time T0 prior to time T1 and time T1, curve T comprises a curve portion of zero slope at T0 and which varies continuously until reaching the value of the slope of curve T at T1. The curve portion before the start of the exposure period imparts a speed other than zero to the grid 7 at the start of the exposure period.

Reduction of the appearance of plates 7a of the grid 7 on the radiographic images by using a time displacement law, as defined by curve T, is most effective and desirably fully effective only if the energy in X-ray form received by the receiver 6 is constant. Blackening of the pixels of the receiver 6 does not depend on the exposure time of the receiver 6, but depends, on the quantity of energy in X-ray form to which each pixel of the receiver 6 has been exposed.

The quantity of energy corresponds to the time integral of the instantaneous energy received by each pixel in X-ray form.

In case the instantaneous energy received is constant, the quantity of energy received is then proportional to the exposure time. The time displacement law is adapted to such theoretical situation. However, the present techniques do not make it possible to obtain an emitter which supplies constant and defined energy in X-ray form.

Figure 4:
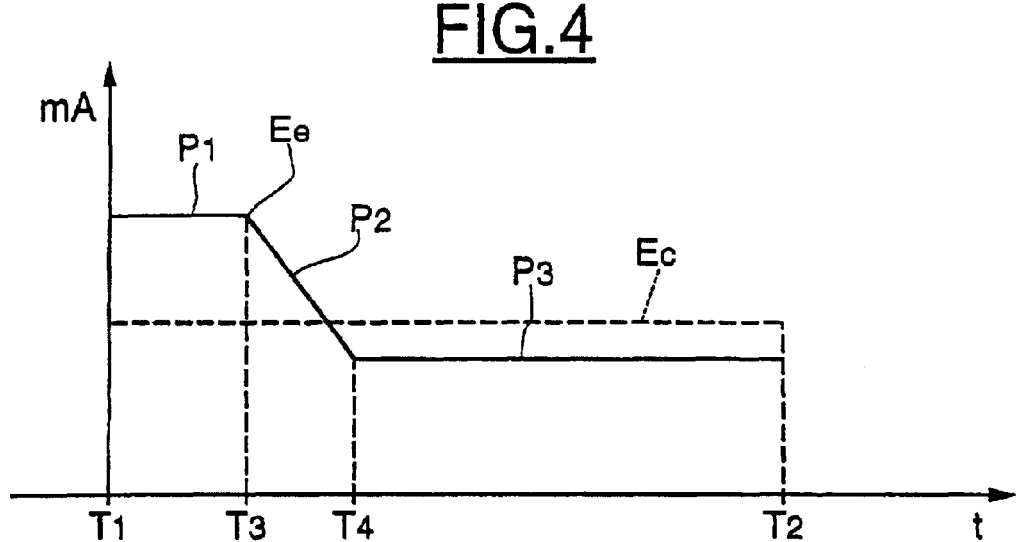
FIG. 4 schematically illustrates the variations of instantaneous energy emitted by the emitter in the form of X-rays.

FIG. 4 schematically illustrates by a solid line the variations of instantaneous energy Ee produced by the emitter 1 as a function of time over an exposure period between times T1 and T2. The constant index value Ec corresponding to the same quantity of energy emitted during the exposure period is represented by a dotted line. The value of the instantaneous energy emitted Ee presents three different segments. In a first period P1 between time T1 and a time T3, the value Ee is constant and higher than the index value Ec. In a second period P2 between time T3 and a time T4, the value Ee steadily diminishes and then remains constant and less than the index value Ec in a period P3 between time T4 and a time T2, which corresponds to the end of the exposure period.

As the instantaneous energy emitted is not constant, the quantity of energy received is not proportional to the elapsed time of the exposure period. In the time interval when the instantaneous energy supplied by the emitter is greater, the quantity of energy to which the pixels of the receiver are exposed is greater. As a result, a difference in exposure time between neighboring pixels due to the period of the grid in motion, during a period of high-energy X-ray emission, entails a greater difference in blackening of neighboring pixels. Visibility of the plates 7a of the grid 7 therefore increases. In a time interval when the energy emitted in X-ray form by the emitter is weaker, the difference in quantity of energy received between neighboring pixels and which is due to the period of the grid in motion is less. Visibility of the plates 7a of the grid 7 diminishes.

In order to reduce the appearance of plates 7a of the grid 7, it would be advisable to define the position of the grid 7 and, therefore, the displacement law, not in relation to time, but in relation to the quantity of energy received or emitted.

The variations of energy emitted in X-ray form by the emitter 1 entail a degradation of quality of the radiographic image obtained and an increase in visibility of the plates 7a of the grid 7. To correct that phenomenon, an embodiment of the invention controls the position and speed of the grid in accordance with a measurement of the energy received by the receiver.

FIG. 3 illustrates an energy law E of displacement of the grid 7 whose reference point position X is shown on the ordinate axis, which expresses the position of the grid 7 as a function of the quantity of energy received by the receiver, shown on the abscissa axis and expressed in milliamperes (mA). The energy law E of displacement is defined solely between positions X0 and XM, which correspond to the beginning and end of the exposure period. In FIG. 3, the energy law E possesses the same profile as the time law T. This corresponds to the time law T in case where the instantaneous energy in X-ray form supplied by the emitter 1 is constant, for example, equal to Ec.

FIG. 1 utilizes a measurement of energy produced by the high-voltage generator, supplied by the means for measurement 12 and which is roughly proportional to the energy received by the receiver 6, and a measurement of energy obtained from a means for measurement 11 placed below the receiver opposite the X-ray beam. The data of these measurements are transmitted to the computer unit 10 which combines them in order to obtain a representative value of the instantaneous energy received by the receiver 6 and of the quantity of energy received by the receiver 6 during the exposure time already elapsed. The central unit 10 utilizes this representative value to transmit a control signal to the means of displacement 8, which results in displacement of the grid 7.

In an alternative embodiment, the means for measurement 14 supplying a measurement of the energy emitted by the emitter 1 in X-ray form could be used alone. As a second alternative embodiment, the means for measurement 13 supplying a measurement of the energy received by the receiver 6 in X-ray form could be used alone.

Before X-ray imaging, an X-ray energy level is selected and the exposure time is determined, which depends on parameters, such as thickness of the object to be X-rayed or energy of the X-rays used. The exposure time is determined to sufficiently blacken the receiver and corresponds to a quantity of energy emitted in X-ray form during a period of exposure sufficient to blacken the receiver properly.

With that exposure time and X-ray energy, the computer unit 10 predefines a time displacement law from the standard time displacement law stored in memory and from an execution program. During the exposure period the rate of displacement of the grid 7 is modified in accordance with the representative value of the energy received in X-ray form by the receiver 6, so that the displacement of the grid 7 as a function of quantity of energy received by the receiver best corresponds to the energy displacement law associated with the predefined time law.

Figure 5:
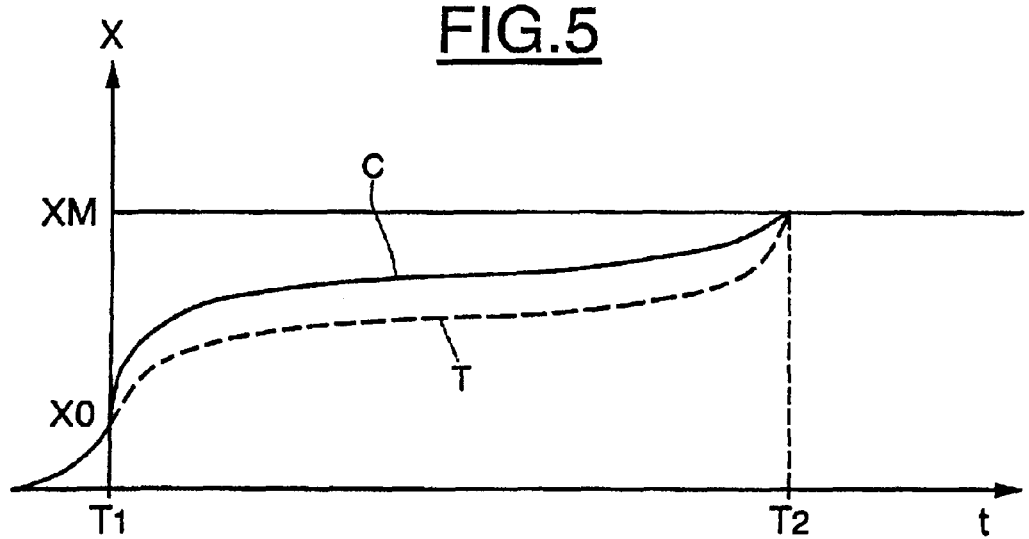
FIG. 5 illustrates a time law corrected as a function of measurement of the energy received by the receiver.

In FIG. 5, the time displacement law T can be seen in a dotted line, predefined from a constant or nominal instantaneous energy received by the receiver 6 of the curve Ec type of FIG. 4, and a time displacement law C corrected according to the measurement of quantity of energy received by the receiver 6 from an instantaneous energy emitted during the exposure period of the curve Ee type of FIG. 4.

Curves Ec and Ee represent the same total quantity of energy emitted during the same exposure time. The instantaneous energy emitted Ee being greater than the index energy Ec in a first time interval, the quantity of energy actually received by the receiver 6 increases more rapidly than the quantity of energy that the receiver 6 would have received if the energy emitted were Ec. The speed of the grid 7 is increased in relation to the speed of the grid 7 according to the time displacement law T, so as to respect the energy displacement law E indicating the position of the grid 7 desired as a function of quantity of energy received. The increase in speed is translated by a slope of curve C steeper than the slope of curve T over the period from T1 to T3.

Over the period from T4 to T2, the instantaneous energy emitted Ee being less than the index energy Ec, the quantity of energy actually received by the receiver 6 increases less rapidly than the quantity of energy that the receiver 6 would have received if the energy emitted were Ec. The speed of the grid 7 is therefore diminished in relation to the time law T, so as to respect the energy displacement law E. The reduction of speed is translated by a slope of curve C less steep than the slope of curve T in proximity to point XM.

In case the exposure time is not known with sufficient precision before the start of the exposure period, it is judicious to modify the time law of reference T and, therefore, the associated energy law during the exposure period, as a function of at least a new exposure time estimate, which depends, for example, on measurement of the instantaneous energy emitted in X-ray form by the emitter 1. For that purpose, the curve defining the reference time law can include several separate parts, some of which retain their profile on the exposure period, while intermediate parts can be modified as a function of the new exposure time estimate, to accelerate or retard displacement of the grid, while maintaining a continuous evolution of the rate of displacement of the grid.

The correction of speed of the anti-scatter grid 7 during the exposure period, taking into account the measurement of energy received by the receiver 6, controls the position of the grid 7 according to the parameter actually determining the blackening of the receiver 6.

Various modifications in structure and/or steps and/or function may be made by one skilled in the art without departing form the scope and extent of the invention as recited in the claims.

What is claimed is:

1. A method for a radiographic imaging of an object by a radiography apparatus having means for providing an X-ray emitter; an anti-scatter grid placed between the object and means for providing a radiographic image receiver, comprising:

displacing the grid in rectilinear translation of the plane of the grid when acquiring the images, between a starting position and an arrival position, according to a predefined time displacement law;

the displacement being at a rate to cause the grid to translate at a greater rate of displacement in proximity to the starting position and to the arrival position than between those two positions; and measuring the energy received in the form of X-rays by the receiver to modify the rate of displacement of the grid at every instant wherein the displacement of the grid is adjusted to the energy received by the means for providing a radiographic image receiver so that, during exposure time each part of the means for providing a radiographic image receiver has been exposed to substantially the same quantity of radiation energy.

2. The method according to claim 1 wherein the energy received in X-ray form by the receiver is measured from the energy emitted by the X-ray emitter.

3. The method according to claim 1 wherein the energy received in the form of X-rays by the receiver is measured from the energy coming to the receiver.

4. The method according to claim 2 wherein the energy received in the form of X-rays by the receiver is measured from the energy coming to the receiver.

5. The method according to claim 1 wherein the displacement of the grid is by other than a whole number of periods, the period being the distance separating an edge of a plate of the grid from an edge of an immediately adjacent plate of the grid.

6. A method for radiographic imaging of an object by a radiography apparatus having means for providing an X-ray emitter, an anti-scatter grid placed between the object and means for providing a radiographic image receiver in rectilinear translation in the plane of the grid when acquiring the images; comprising:

displacing the grid; the displacement of the grid being in accordance with a modification of a rate of displacement and;

measuring the energy received in the form of X-rays by the receiver to modify the rate of displacement of the grid at every instant wherein the displacement of the grid is adjusted to the energy received by the means for providing a radiographic image receiver so that during exposure time each part of the means for providing a radiographic image receiver has been exposed to substantially the same quantity of radiation energy.

7. The method according to claim 6 wherein the energy received in X-ray form by the receiver is measured from the energy emitted by the X-ray emitter.

8. The method according to claim 7 wherein the energy received in the form of X-ray; by the receiver is measured from the energy coming to the receiver.

9. The method according to claim 6 wherein the energy received in the form of X-rays by the receiver is measured from the energy coming to the receiver.

10. The method according to claim 6 wherein the displacement of the grid is by other than a whole number of periods, the period being the distance separating an edge of a plate of the grid from an edge of an immediately adjacent plate of the grid.

11. A method for radiographic imaging of an object by a radiography apparatus having means for providing an X-ray emitter, an anti-scatter grid placed between the object and means for providing a radiographic image receiver in rectilinear translation in the plane of the grid when acquiring the images comprising:

displacing the grid, the displacement or the grid being in accordance with a modification of a rate of displacement and;

the displacement of the grid is by other than a whole number of periods, the period being the distance separating an edge of a plate of the grid from an edge of an immediately adjacent plate of the grid; and measuring the energy received in the form of X-rays by the receiver to modify the rate of displacement of the grid at every instant.

12. A radiographic imaging device comprising:

means for providing an X-ray emitter;

means for providing a receiver of X-rays after having crossed an object to be studied;

an anti-scatter grid moveable in translation in a plane roughly perpendicular to the X-rays;

means for computing;

means for providing for displacement of the anti-scatter grid in translation in its plane when acquiring of the image, between a starting position and an arrival position;

means for measurement of the energy received by the means for providing a receiver in the form of X-rays; and means for modifying a predefined time displacement law determined by the means for computing, the means for computing connected to the means for measurement of the energy received by the means for providing a receiver and providing a control signal to the means for displacement.

13. The device according to claim 12 wherein the means for measurement is disposed on an energy supply link of the means for providing an emitter.

14. The device according to claim 13 wherein means for measurement is situated on the means for providing a receiver.

15. The device according to claim 12 wherein means for measurement is situated on the means for providing a receiver.

16. The device of claim 12 wherein the means for modifying comprises controlling the time displacement law to modify the rate of displacement of the grid at every instance.

17. The device of claim 12 wherein the means for modifying comprises controlling the time displacement law to modify the rate of displacement of the grid at a greater rate of displacement in proximity to a starting position and an arrival position then between the two positions.

18. The device according to claim 12 wherein data received by the means for computing from the means for measurement corrects the speed of the grid.

* * * * *